United States Patent [19]

Hamilton et al.

[11] 4,105,849
[45] Aug. 8, 1978

[54] [(SUBSTITUTED)PHENYL]PHENYLMETHYL-1-(DIALKYLAMINOALKYL)PIPERIDINES

[75] Inventors: Robert W. Hamilton, Wilmette; Kurt J. Rorig, Glenview, both of Ill.

[73] Assignee: G. D. Searle & Co., Chicago, Ill.

[21] Appl. No.: 510,745

[22] Filed: Sep. 30, 1974

[51] Int. Cl.² .................. C07D 413/06; C07D 211/28; A61K 31/535; A61K 31/445
[52] U.S. Cl. .............................. 544/129; 260/293.64; 260/293.78; 424/248.56; 424/267
[58] Field of Search ............... 260/247.5 G, 293.64, 260/293.78; 544/129

[56]  References Cited
U.S. PATENT DOCUMENTS

| 3,081,303 | 3/1963 | Rorig | 260/247.5 G |
| 3,806,526 | 4/1974 | Carr | 260/247.5 G |
| 3,862,173 | 1/1975 | Carr | 260/247.5 G |
| 3,878,217 | 4/1975 | Carr | 260/293.64 |

*Primary Examiner*—James O. Thomas, Jr.
*Assistant Examiner*—Michael Shippen
*Attorney, Agent, or Firm*—John J. McDonnell

[57]  ABSTRACT

The present invention relates to compounds of the formula

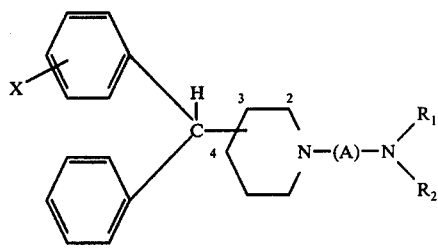

having the [(X-substituted)phenyl]phenylmethyl moiety attached to the 2, 3, or 4 position of the piperidine ring and wherein X is hydrogen, halo, trifluoromethyl, (lower alkyl) containing 1-7 carbon atoms, or (lower alkoxy) containing 1-7 carbon atoms, A represents alkylene containing 1-3 carbon atoms, and $R_1$ and $R_2$ represent (lower alkyl) containing 1-7 carbon atoms or $R_1$ and $R_2$ together with N represent piperidino or morpholino and the pharmaceutically acceptable salts thereof. The compounds of this invention are prepared by the reaction of an appropriate [(X-substituted)-phenyl]phenylmethylpiperidine with an appropriate 1-halo-2-dialkylaminoalkane. The compounds of this invention are useful as anti-arrythmic agents.

5 Claims, No Drawings

[(SUBSTITUTED)PHENYL]PHENYLMETHYL-1-(DIALKYLAMINOALKYL)PIPERIDINES

The present invention relates to compounds of the following structure:

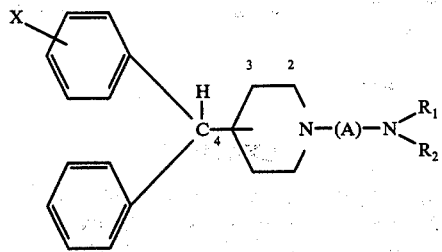

wherein the

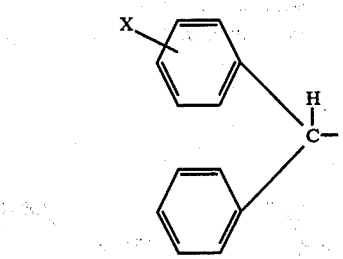

moiety is attached at 2, 3 or 4 and wherein X represents hydrogen, halo, trifluoromethyl, (lower alkyl) containing 1-7 carbon atoms or (lower alkoxy) containing 1-7 carbon atoms, A represents alkylene containing 1-3 carbon atoms, and $R_1$ and $R_2$ represent (lower alkyl) containing 1-7 carbon atoms or $R_1$ and $R_2$ together with N represent piperidino or morpholino and the pharmaceutically acceptable acid addition salts thereof. Fluoro, chloro, bromo, and iodo are suitable halos. Ethylene, propylene, isopropylene are suitable alkylenes with ethylene being preferred. Methoxy and ethoxy are preferred alkoxy and methyl, ethyl and isopropyl are preferred lower alkyl.

The organic bases of this invention form nontoxic, acid-addition salts with a variety of organic and inorganic acids. Such salts are formed with acids such as sulfuric, phosphoric, hydrochloric, hydrobromic, hydroiodic, sulfamic, citric, lactic, maleic, malic, succinic, tartaric, clinnamic, acetic, benzoic, gluconic, ascorbic, and related acids.

The compounds of the present invention are structurally distinct from those of the prior art. The structural distinctions between the compounds of the present invention and those of the prior art are illustrated by considering the following structure:

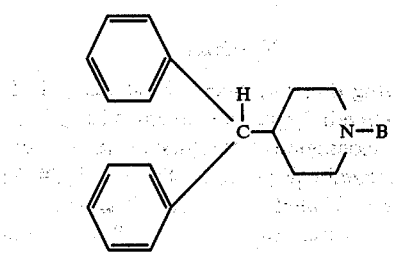

Compounds in which B in the above structure is alkyl are described in U.S. Pat. No. 2,739,968 and compounds in which B is

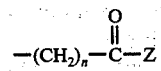

wherein Z represents thienyl, phenyl or substituted phenyl are described in U.S. Pat. No. 3,806,526. In contrast, in compounds of the present invention B is dialkylaminoalkyl, morpholinoalkyl or piperidinoalkyl. U.S. Pat. No. 3,267,108 describes compounds in which B is hydrogen or amino. Belgium Pat. No. 649,848 describes piperazino compounds of the following general structure.

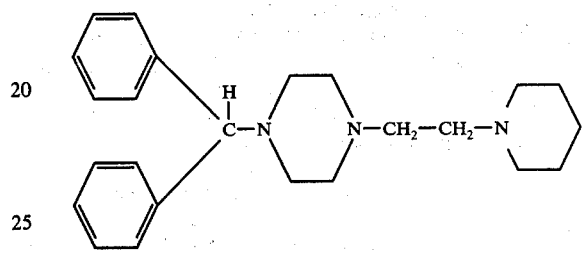

The compounds of the present invention are distinguished in that the diphenylmethyl is attached to a carbon instead of nitrogen as in the prior art piperazino compounds.

Compounds of the present invention are prepared by reacting an appropriate [(X-substituted)phenyl]phenylmethylpiperidine with an appropriate β-dialkylamino halide as set out in Scheme I Scheme I

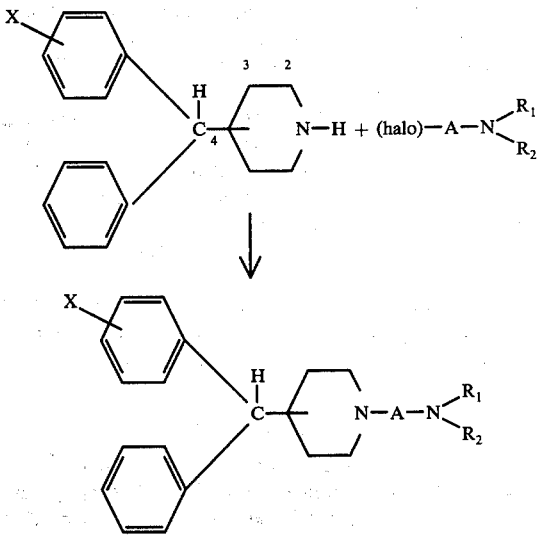

Scheme I

X, A, $R_1$, $R_2$ and halo are as previously defined.

Following Scheme I, 18.1 parts of 4-diphenylmethylpiperidine (U.S. Pat. No. 3,806,526) 13.6 parts of 2-chloroethylpiperidine hydrochloride and 16 parts of sodium carbonate are placed in 250 parts of aqueous 95% ethanol and heated at reflux for 5 hours with stirring. The ethanol is removed to provide an oil which is 1-(2-piperidinoethyl)-4-(diphenylmethyl)piperidine.

This oil is dissolved in anhydrous ethanol and 2 equivalents of hydrochloric acid gas are added to provide 1-(2-piperidinoethyl)-4-(diphenylmethyl)piperidine dihydrochloride, melting at 330° C. The anhydrous ethanol solution of 1-(2-piperidinoethyl)-4-(diphenylmethyl)piperidine is reacted with 1.5 equivalents of oxalic acid to provide the oxalic acid salt. In a similar manner other previously mentioned pharmaceutically acceptable salts are formed.

The antiarrhythmic utility of the instant compounds is evident from the results of a standardized test for their capacity to slow the ventricular tachycardia induced by aconitine in the isolated rabbit heart. The procedure is essentially that described by Lucchesi [J. Pharmacol. Exp. Therap., 137, 291 (1962)], modified in certain particulars as follows: Hearts are obtained from adult albino rabbits of either sex and perfused in apparatus modeled after that devised by Anderson and Craver [J. Pharmacol. Exp. Therap., 93, 135 (1948)]. Composition of the perfusion solution is the same as Lucchesi's, but the volume is increased to 200 ml. and the temperature lowered to 28°. Aconitine (ordinarily as the nitrate) is administered as soon as the heart beat is regular and the EKG pattern normal, the dose being so selected as to at least double the rate. Typically, 0.05 ml. of 0.1% aconitine nitrate in physiological saline is injected. EKG's are recorded at 5 minute intervals after onset of ventricular tachycardia until two successive readings show stabilization of the rate. Perfusate collected during this time is discarded and replaced with fresh solution q.s. 200 ml. Promptly following stabilization, 2 mg. of compound dissolved or suspended in 1 ml. of physiological saline, is mixed with the perfusion solution. Ten minutes later a like amount is introduced, followed after a further ten minutes by double the first amount. Final concentration of compound in the perfusion solution is thus 40 mg. per 1. Recording of EKG's is continued at 5 minute intervals throughout this time and for 10 minutes thereafter. A compound is considered antiarrhythmic if, at any time during the 30 minutes immediately following initial administration in at least half of a minimum of two test, it reduces by 50% or more the rate recorded 10 minutes after onset of tachycardia.

The invention will appear more fully by the examples which follow. These examples are given by way of illustration only and are not to be construed as limiting the invention either in spirit or in scope, as many modifications both in materials and methods will be apparent to those skilled in the art. In these examples, temperatures are given in degrees centigrade (°C.) and quantities of materials are expressed in parts by weight unless otherwise specified. The relationship between parts by weight and parts by volume is the same as that existing between grams and milliliters.

EXAMPLE 1

18.1 parts of 4-diphenylmethylpiperidine (U.S. Pat. No. 3,806,526) 13.6 parts of 1-(2-chloroethyl)piperidine hydrochloride and 16 parts of sodium carbonate are placed in 250 parts of aqueous 95% ethanol and heated at reflux for 5 hours with stirring. The ethanol is removed to provide a residue. The residue is partitioned in ether and water to remove salts. The ethereal layer is separated and the ether is removed to give 4-(diphenylmethyl)piperidine as an oil. This oil is dissolved in anhydrous ethanol and 2 equivalents of hydrochloric acid gas are added to the solution and then anhydrous ether is added to precipitate 1-(2-piperidinoethyl)-4-(diphenylmethyl)piperidine dihydrochloride, melting at 330° C. This compound has the following structural formula:

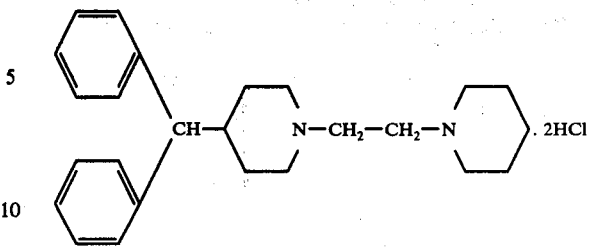

EXAMPLE 2

Following the procedure in Example 1, 18.1 parts of 4-diphenylmethylpiperidine and 14.8 parts of 2-chloro-1-diisopropylaminoethane hydrochloride are converted to 1-(2-diisopropylaminoethyl)-4-(diphenylmethyl)piperidine and then to 1-(2-diisopropylaminoethyl)-4-(diphenylmethyl)piperidine dihydrochloride, melting at 144°-5° C. This compound has the following structural formula

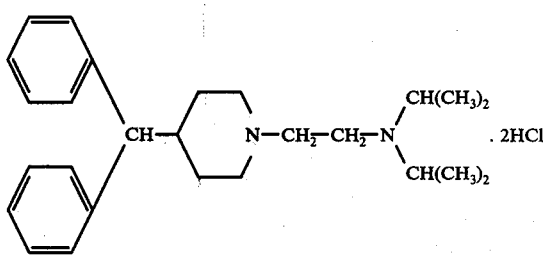

EXAMPLE 3

Following the procedure in Example 1, 18.1 parts of 4-diphenylmethylpiperidine and 10.6 parts of 2-chloro-1-dimethylaminoethane hydrochloride are converted to 1-(2-dimethylaminoethyl)-4-(diphenylmethyl)piperidine and then to 1-(2-dimethylaminoethyl)-4-(diphenylmethyl)piperidine dihydrochloride, melting at 278°-281° C. This compound has the following structural formula

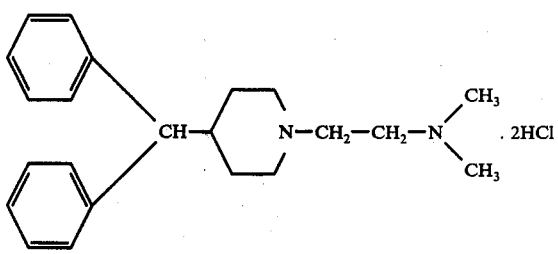

EXAMPLE 4

Following the procedure in Example 1, 18.1 parts of 4-diphenylmethylpiperidine and 14 parts of 2-chloro-1-diethylaminoethane hydrochloride are converted to 1-(2-diethylaminoethyl)-4-(diphenylmethyl) piperidine and then to 1-(2-diethylaminoethyl)-4-piperidine dihydrochloride, melting at 235°-7° C. This compound has the following structural formula

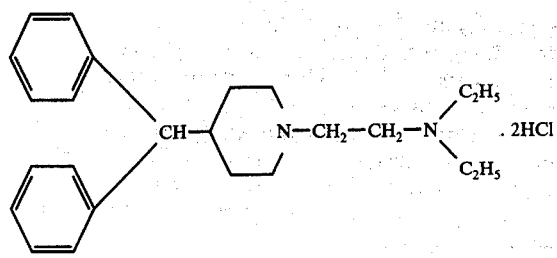

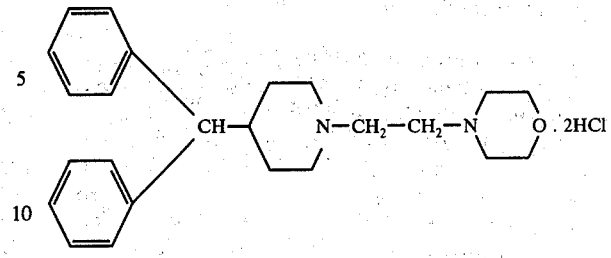

Example 5

Following the procedure in Example 1, 20.6 parts of 4-(chlorophenylphenylmethyl)piperidine and 14 parts of 2-chloro-1-diethylaminoethane hydrochloride are converted to 1-(2-diethylaminoethyl)-4-[(4-chlorophenyl)phenylmethyl]piperidine and then to 1-(2-diethylaminoethyl)-4-[(4-chlorophenyl)phenylmethyl]piperidine dihydrochloride, melting at 222°–4° C. This compound has the following structural formula

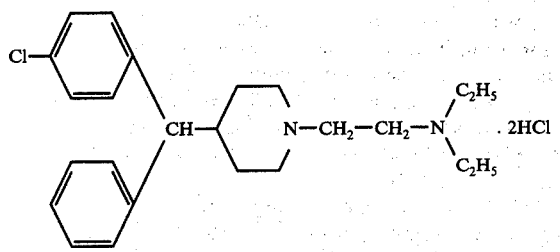

EXAMPLE 6

Following the procedure in Example 1, 18.1 parts of 4-diphenylmethylpiperidine and 14 parts of 3-chloro-1-diethylaminopropane hydrochloride are converted to 1-diethylaminopropyl-4-diphenylmethylpiperidine and then to 1-diethylaminopropyl-4-diphenylmethylpiperidine dihydrochloride, melting at 235°–6° C. This compound has the following structural formula

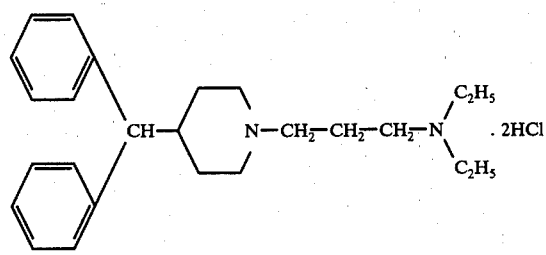

EXAMPLE 7

Following the procedure in Example 1, 18.1 parts of 4-diphenylmethylpiperidine and 13.8 parts of N-(2-chloroethyl)morpholine hydrochloride are converted to 1-(2-morpholinoethyl)-4-diphenylmethylpiperidine and then to 1-(2-morpholinoethyl)-4-diphenylmethylpiperidine dihydrochloride, melting at 320° C. This compound has the following structural formula

EXAMPLE 8

Following the procedure in Example 1, 20.6 parts of 3-(4-chlorophenyl)phenylmethylpiperidine and 13.8 parts of N-(2-chloroethyl)morpholine hydrochloride are converted to 1-(2-morpholinoethyl)-3-[(4-chlorophenyl)phenylmethyl]piperidine and then to 1-(2-morpholinoethyl)-3-[(4-chlorophenyl)phenylmethyl]piperidine dihydrochloride, melting at 259°–62° C. This compound has the following structural formula

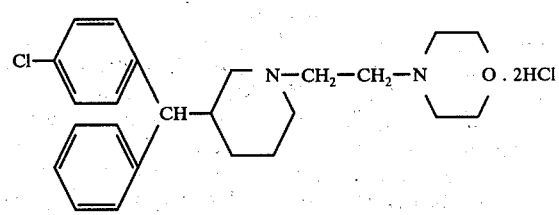

EXAMPLE 9

Following the procedure in Example 1, 18.1 parts of 2-diphenylmethylpiperidine and 13.8 parts of N-(2-chloroethyl)morpholine hydrochloride are converted to 1-(2-morpholinoethyl)-2-diphenylmethylpiperidine and then to 1-(2-morpholinoethyl)-2-diphenylmethylpiperidine dihydrochloride, melting at 249°–53° C. This compound has the following structural formula

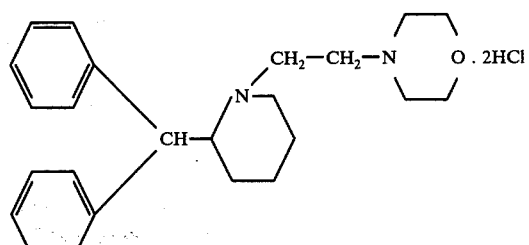

EXAMPLE 10

To a solution of 92 parts of 4-benzoylpyridine in 800 parts of ether is added, during 1 hour with continuous agitation at room temperatures, a solution of 118 parts of p-trifluoromethylphenyl magnesium bromide in 300 parts of ether. To the resultant mixture is added a solution of 104 parts of ammonium chloride in 416 parts of water. The ether layer is separated and extracted with dilute hydrochloric acid. The extract is rendered alkaline by addition of aqueous sodium hydroxide and then extracted with ether. This extract is dried over potassium carbonate. Cooling provides α-(p-trifluoromethyl)-α-phenyl-α-(4-pyridyl)methanol, melting at 164°-5° C.

B. A mixture of 33 parts of α-(p-trifluoromethyl)-α-phenyl-α-(4-pyridyl)methanol, 60 parts of glacial acetic acid, 18 parts of concentrated hydrochloric acid, and 60 parts of 47% hydriodic acid is heated at the boiling point under reflux for 2 minutes, then thoroughly mixed into a solution of 24 parts of sodium hydrosulfate in 180 parts of water. The resultant mixture is made alkaline with sodium hydroxide and then extracted with ether. The ether extract is dried over anhydrous potassium carbonate and the filtrate is cooled to provide 4-[α-(p-trifluoromethylphenyl) benzyl]pyridine.

A solution of 15.7 parts of 4-[α-(p-trifluoromethylphenyl)benzyl]pyridine in 250 parts of acetic acid is heated, with agitation, at 47° C. under approximately 4 atmospheres of hydrogen and in the presence of 2 parts of platinum oxide catalyst for 2 hours. The resultant mixture is filtered, and the filtrate is stripped of solvent by vacuum distillation. The residue is poured into 3 volumes of ice water, and the mixture thus obtained is made alkaline with sodium hydroxide. This mixture is then extracted with ether. The ether extract is dried over anhydrous potassium carbonate, filtered, and the ether removed to provide 4-[(4-trifluoromethylphenyl)-phenylmethyl]piperidine as an oil.

C. Following the procedure in Example, 1, 23 parts of 4-[(4-trifluoromethylphenyl)phenylmethyl]piperidine and 14 parts of 1-chloro-2-diethylaminoethane hydrochloride are converted to 1-(2-diethylaminoethyl)-4-[(4-trifluoromethylphenyl)phenylmethyl]piperidine and then to 1-(2-diethylaminoethyl)-4-[(4-trifluoromethylphenyl)phenylmethyl]piperidine dihydrochloride, melting at 222°-25° C. This compound has the following structural formula

EXAMPLE 11

Following the procedure in Example 12, 23 parts of 4-[(4-trifluoromethylphenyl)phenylmethyl]piperidine and 13.8 parts or N-β-chloroethylmorpholine hydrochloride are converted to 1-(2-morpholinoethyl)-4-[(4-trifluoromethylphenyl)phenylmethyl]piperidine, and then to 1(2-morpholinoethyl)-4-[(4-trifluoromethylphenyl)phenylmethyl]piperidine dihydrochloride, melting at 308°-310° C. This compound has the following structural formula

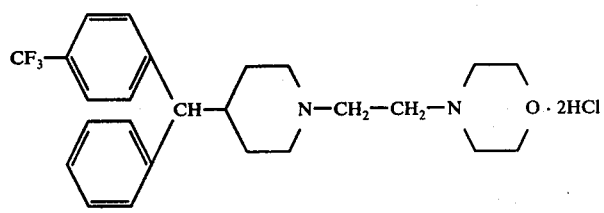

EXAMPLE 12

Following the procedure in Example 10A, 92 parts of 4-benzoylpyridine and 118 parts of p-methoxy-phenyl magnesium bromide is converted to α-p-methoxy-phenyl-α-phenyl-α-4-pyridylmethanol. 33 Parts of the latter compound is converted to 4[α-(p-methoxylphenyl)-benzyl]pyridine and in turn reduced to 4-[(p-methoxyphenyl)phenylmethyl]piperidine by the procedures set out in Example 10B.

20.2 Parts of the latter compound and 13.8 parts of N-β-chloroethylmorpholine hydrochloride are converted to 1-(2-morpholinoethyl)-4-[(4-methoxyphenyl)-phenylmethyl]piperidine and then converted to the 1-(2-morpholinoethyl)-4-[(4-methoxyphenyl)phenylmethyl]piperidine dihydrochloride, melting at 298° C. This compound has the following formula

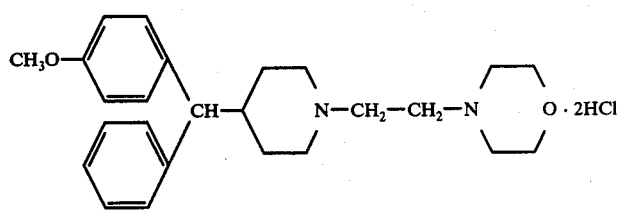

EXAMPLE 13

Following the procedure in Example 1, 20.6 parts of 4-(4-chlorophenyl)phenylmethylpiperidine and 13.8 parts of N-(2-chloroethyl)morpholine hydrochloride are converted to 1-(2-morpholinoethyl)-4-[(4-chlorophenyl)phenylmethyl]piperidine and then to 1-(2-morpholinoethyl)-4-[(4-chlorophenyl)phenylmethyl]piperidine dihydrochloride, melting at 290°-291° C. This compound has the following structural formula

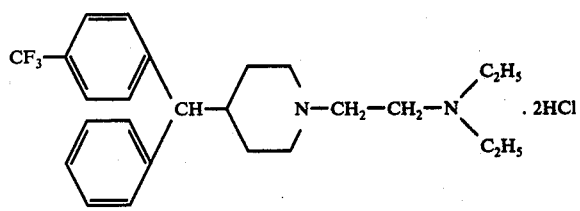

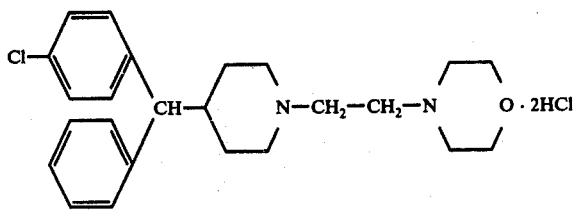

What is claimed is:
1. A compound of the formula

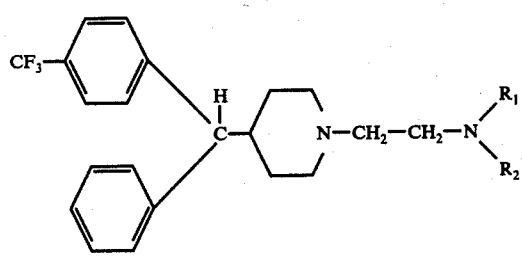

wherein $R_1$ and $R_2$ represent lower alkyl having 1-7 carbon atoms or $R_1$ and $R_2$ together with N represent piperidino or morpholino and the pharmaceutically acceptable acid addition salts thereof.

2. According to claim 1, the compound which is 1-(2-diethylaminoethyl)-4-[(4-trifluoromethylphenyl)-phenylmethyl]piperidine.

3. According to claim 1, the compound which is 1-(2-diethylaminoethyl)-4-[(4-trifluoromethylphenyl)phenylmethyl]piperidine dihydrochloride.

4. According to claim 1, the compound which is 1-(2-morpholinoethyl)-4-[(4-trifluoromethylphenyl)-phenylmethyl]piperidine.

5. According to claim 1, the compound which is 1-(2-morpholinoethyl)-4-[(4-trifluoromethylphenyl)-phenylmethyl]piperidine dihydrochloride.

* * * * *